United States Patent [19]

Beck

[11] B 3,989,718

[45] Nov. 2, 1976

[54] [1]BENZOTHIENO[3,2-B]FURANS

[75] Inventor: James Richard Beck, Indianapolis, Ind.

[73] Assignee: Eli Lilly and Company, Indianapolis, Ind.

[22] Filed: May 6, 1975

[21] Appl. No.: 574,996

[44] Published under the second Trial Voluntary Protest Program on February 17, 1976 as document No. B 574,996.

[52] U.S. Cl. .............................. 260/330.5; 424/275; 260/999
[51] Int. Cl.$^2$ ....................................... C07D 333/60
[58] Field of Search ................................. 260/330.5

[56] References Cited
UNITED STATES PATENTS

| | | | |
|---|---|---|---|
| 3,499,894 | 3/1970 | Bockstahler | 260/247.1 |
| 3,659,004 | 4/1972 | Wagner et al. | 260/330.5 |
| 3,663,568 | 5/1972 | Roos et al. | 260/330.5 |
| 3,706,747 | 12/1972 | DeAngelis et al. | 260/265.5 R |
| 3,772,336 | 11/1973 | Wright | 260/330.5 |
| 3,803,180 | 4/1974 | Berger et al. | 260/346.2 M |

OTHER PUBLICATIONS

Friedlander, Chem. Ber. 32: 121 (1899).
Schroeder, et al., J. Org. Chem. 27: 586–591 (1962).
Beck, J. Org. Chem. 38: 4086 (1973).

*Primary Examiner*—Henry R. Jiles
*Assistant Examiner*—C. M. S. Jaisle
*Attorney, Agent, or Firm*—Joseph A. Jones; Everet F. Smith

[57] ABSTRACT

A new class of organic chemical compounds [1]benzothieno[3,2-b]furans, are made by O-alkylation of 3-hydroxybenzo[b]thiophene-2-carboxylates with alkyl haloacetates, haloacetonitriles or α-halomethyl alkyl ketones, followed by cyclization of the intermediate products with alkali metals or alkali metal alkoxides. The compounds are antimicrobials.

5 Claims, No Drawings

[1]BENZOTHIENO[3,2-B]FURANS

BACKGROUND OF THE INVENTION

This invention belongs to the field of synthetic organic chemistry and provides to the art a new series of antimicrobial heterocyclic compounds.

The 3-hydroxybenzo[b]thiophene-2-carboxylates which are starting compounds for the compounds of this invention were disclosed by Beck, J. Org. Chem. 38, 4086 (1973). Such compounds were first synthesized by Friedlander, Justus Liebigs Ann. Chem. 351, 390 (1906).

Additional references which relate to the synthesis of benzo[b]thiophenes include Wagner, U.S. Pat. No. 3,659,004, Roos, U.S. Pat. No. 3,663,568, and De Angelis, U.S. Pat. No. 3,706,747.

The background of this invention also includes the prior art synthesis of benzofurans with alkoxides as reagents. References on the synthesis include Friedlander, Chem. Ber. 32, 1867 (1899) and Schroeder et al., J. Org. Chem. 27, 586 (1962).

De Angelis, U.S. Pat. No. 3,706,747, disclosed benzothieno[3,2-d]pyrimidines and benzofuro[3,2-d]pyrimidines which are also relevant to the background of this invention.

SUMMARY OF THE INVENTION

The present invention provides to organic chemists new compounds of the formula

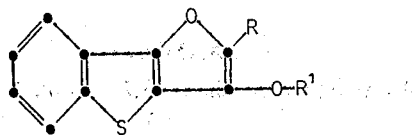

wherein R represents cyano, $C_1$–$C_2$ alkylcarbonyl or $C_1$–$C_2$ alkoxycarbonyl;
$R^1$ represents $C_1$–$C_2$ alkyl or hydrogen;
provided that $R^1$ represents hydrogen when R represents cyano or $C_1$–$C_2$ alkylcarbonyl.

DESCRIPTION OF THE PREFERRED EMBODIMENT

In the above general formula, the terms $C_1$–$C_2$ alkyl, $C_1$–$C_2$ alkylcarbonyl and $C_1$–$C_2$ alkoxycarbonyl refer to such chemical groups as methyl, ethyl, acetyl, propionyl, methoxycarbonyl and ethoxycarbonyl.

The following compounds are named to assure that organic chemists understand the invention. The compounds are not intended to, and should not be understood to, bound the scope of the invention.

3-hydroxy[1]benzothieno[3,2-b]furan-2-carboxylic acid, methyl ester
3-hydroxy[1]benzothieno[3,2-b]furan-2-carbonitrile
3-hydroxy[1]benzothieno[3,2-b]furan-2-yl ethyl ketone
3-methoxy[1]benzothieno[3,2-b]furan-2-carboxylic acid, methyl ester
3-methoxy[1]benzothieno[3,2-b]furan-2-carboxylic acid, ethyl ester
3-hydroxy[1]benzothieno[3,2-b]furan-2-carboxylic acid, ethyl ester
3-ethoxy[1]benzothieno[3,2-b]furan-2-carboxylic acid, methyl ester
3-ethoxy[1]benzothieno[3,2-b]furan-2-carboxylic acid, ethyl ester
3-hydroxy[1]benzothieno[3,2-b]furan-2-yl methyl ketone The starting compounds in the synthesis of compounds of this invention are 3-hydroxybenzo[b]thiophene-2-carboxylates, the synthesis of which was taught by Beck, supra. Such compounds are readily prepared by the reaction at a temperature from ice bath temperature to ambient of an o-nitrobenzoate and an alkylmercaptoacetate in dimethylformamide in the presence of an inorganic base such as an alkali metal hydroxide. Example 1 below illustrates the synthesis of a typical starting compound.

Synthesis of the new compounds proceeds in two and sometimes three steps. In the first step, the 3-hydroxybenzothiophene is O-alkylated with a derivative of α-haloacetic acid which is chosen depending on the R substituent of the desired product. If R is an alkoxycarbonyl group, the first reactant is an alkyl 2-haloacetate; if R is cyano, the reactant is a haloacetonitrile; and if R is alkylcarbonyl, the reactant is an alkyl halomethyl ketone.

In the second step of the synthesis, the intermediate product is cyclized by treatment with an alkali metal or an alkali metal alkoxide such as sodium methoxide or potassium t-butoxide at a temperature from ambient temperature to the reflux temperature of the reaction solvent, which is chosen from among the aromatic solvents and the lower alkanols. The cyclization step produces the compounds of the invention wherein $R^1$ represents hydrogen in good yields in the range of 60–90 percent. When a 3-alkoxy compound is to be made, the 3-hydroxy group is easily alkylated with a reagent such as dialkyl sulfate or an alkyl halide in the presence of an alkali metal alkoxide or hydroxide.

The following preparative examples are shown to assure that organic chemists can easily prepare the compounds of this invention.

EXAMPLE 1 methyl 3-hydroxybenzo[b]thiophene-2-carboxylate

A 5.4 g. portion of methyl o-nitrobenzoate and 2.7 g. of methyl mercaptoacetate were dissolved in 60 ml. of dimethylformamide at ice bath temperature, and 2.5 g. of lithium hydroxide was added slowly with stirring. The mixture was stirred at ice bath temperature for 30 minutes, and then at room temperature for 2.5 hours. The reaction mixture was then poured into ice water and the aqueous mixture was acidified with dilute HCl. The mixture was then filtered, and the collected solids were dried and crystallized from aqueous ethanol to produce 3.7 g. of methyl 3-hydroxybenzo[b]thiophene-2-carboxylate, m.p. 109°–110°C.

The following three examples illustrate the first step in the syntheses of the new compounds. Examples 2, 3 and 4 show, respectively, intermediate products suitable for the preparation of compounds wherein R represents cyano, alkylcarbonyl and alkoxycarbonyl.

EXAMPLE 2

3-(ayanomethoxy)benzo[b]thiophene-2-carboxylic acid, methyl ester

A solution was made of 12.6 g. of the product of Example 1 and 8.1 g. of potassium t-butoxide in 100 ml. of dimethyl sulfoxide. To the solution was added, dropwise with stirring, 12 ml. of chloroacetonitrile. The reaction mixture was heated at steam bath temperature for one hour and poured into ice water, and the solid crude product was collected by filtration. The crude product was crystallized from ethanol to yield 12.6 g. of 3-(cyanomethoxy)benzo[b]-thiophene-2-carboxylic acid, methyl ester, m.p. 123°–24°C. The product was identified by nuclear magnetic resonance analysis and by elemental microanalysis as follows.

|   | Theoretical | Found |
|---|---|---|
| C | 58.29% | 58.37% |
| H | 3.67 | 3.86 |
| N | 5.66 | 5.85 |
| S | 12.97 | 12.88 |

EXAMPLE 3

3-(acetylmethoxy)benzo[b]thiophene-2-carboxylic acid, methyl ester

To a solution of 12.6 g. of the product of Example 1 and 8.1 g. of potassium t-butoxide in 100 ml. of dimethyl sulfoxide was added, dropwise with stirring, 15 ml. of chloroacetone. The mixture was treated and the product was recovered as shown in Example 2, except that the product was crystallized from ethanol-water. The product was 10.7 g. of 3-(acetlymethoxy)benzo[b]thiophene-2-carboxylic acid, methyl ester, m.p. 57°–58°C. It was identified by NMR analysis and elemental microanalysis as follows.

|   | Theoretical | Found |
|---|---|---|
| C | 59.08% | 58.91% |
| H | 4.58 | 4.86 |
| S | 12.13 | 12.42 |

EXAMPLE 4

3-(carboxymethoxy)benzo[b]thiophene-2-carboxylic acid, dimethyl ester

The reaction was performed according to the scheme of Example 3, except that the alkylating agent was 14 ml. of methyl 2-chloroacetate. The crude product was crystallized from alcohol to yield 15.7 g. of 3-(carboxymethoxy)benzo[b]thiophene-2-carboxylic acid, dimethyl ester, m.p. 98°–99°C. which was identified by NMR analysis and elemental microanalysis.

|   | Theoretical | Found |
|---|---|---|
| C | 55.71% | 55.59% |
| H | 4.32 | 4.58 |
| S | 11.44 | 11.40 |

The following four examples illustrate the cyclization of the intermediate products to form the new compounds of this invention.

EXAMPLE 5

3-hydroxy[1]benzothieno[3,2-b]furan-2-carboxylic acid, methyl ester

A solution containing 5.1 g. of 3-(carboxymethoxy)benzo[b]thiophene-2-carboxylic acid, dimethyl ester, and 2.7 g. of potassium t-butoxide in 100 ml. of benzene was stirred at reflux temperature for 2.5 hours. The mixture was cooled and extracted with 100 ml. of water. The aqueous phase was washed with benzene, and was then acidified. The crude solid was collected by filtration and crystallized from methanol-water to yield 3.8 g. of 3-hydroxy[1]benzothieno[3,2-b]furan-2-carboxylic acid, methyl ester, m.p. 124°–25°C. The product was identified by NMR analysis, IR analysis and elemental microanalysis.

|   | Theoretical | Found |
|---|---|---|
| C | 58.05% | 57.87% |
| H | 3.25 | 3.29 |
| S | 12.92 | 12.76 |

EXAMPLE 6

3-hydroxy[1]benzothieno[3,2-b]furan-2-carbonitrile

A solution of 7.4 g. of 3-(cyanomethoxy)-benzo[b]-thiophene-2-carboxylic acid, methyl ester and 4.0 g. of potassium t-butoxide in 100 ml. of benzene was reacted and the product was isolated as shown in the example above. The product was 5.45 g. of 3-hydroxy[1]benzothieno[3,2-b]-furan-2-carbonitrile, m.p. 174°–75°C. It was identified as in the example above, and the elemental microanalysis was as follows.

|   | Theoretical | Found |
|---|---|---|
| C | 61.39% | 61.21% |
| H | 2.34 | 2.60 |
| N | 6.51 | 6.29 |
| S | 14.90 | 14.62 |

EXAMPLE 7

3-hydroxy[1]benzothieno[3,2-b]furan-2-yl methyl ketone

A solution of 2.6 g. of 3-(acetylmethoxy)benzo[b]thiophene-2-carboxylic acid, methyl ester, and 0.65 g. of sodium methoxide in 50 ml. of methanol was stirred at room temperature for 4 hours. The reaction mixture was poured into ice water and acidified with dilute HCl. The crude solid was collected and crystallized from ethanol to yield 1.5 g. of 3-hydroxy[1]benzothieno[3,2-b]furan-2-yl methyl ketone, m.p. 196°–97°C., which was identified as above. The following elemental microanalysis was obtained.

|   | Theoretical | Found |
|---|---|---|
| C | 62.06% | 61.78% |
| H | 3.47 | 3.37 |
| S | 13.81 | 13.53 |

EXAMPLE 8

3-methoxy[1]benzothieno[3,2-b]furan-2-carboxylic acid, methyl ester

A 10 ml. portion of dimethyl sulfate was added dropwise to a solution containing 5 g. of 3-hydroxy[1]benzothieno[3,2-b]furan-2-carboxylic acid, methyl ester, and 2.7 g. of potassium t-butoxide in 60 ml. of dimethyl sulfoxide. The mixture was stirred at room temperature for an hour after the completion of the addition. The reaction mixture was then poured into ice water, and the solids were collected by filtration and crystallized from ethanol to yield 3.9 g. of 3-methoxy[1]benzothieno[3,2-b]furan-2-carboxylic acid, methyl ester, m.p. 145°–46°C. The product was identified as described above with the following elemental microanalysis results.

|   | Theoretical | Found |
|---|---|---|
| C | 59.53% | 59.41% |
| H | 3.84 | 3.88 |
| S | 12.22 | 12.34 |

The compounds of this invention have valuable antimicrobial activity. For example, the compounds have been shown to be effective inhibitors of the replication of harmful microorganisms such as *Aspergillus flavus*, *Bordetella bronchiseptica*, *Ceratocystis ulmi*, *Proteus morganii*, *Staphylococcus aureus*, *Trichophyton mentagrophytes*, *Erwinia amylovora* and *Streptococcus faecalis*. Thus, the compounds may be used for the sterilization and cleansing of surfaces and areas such as hospital environments, kitchen environments and household walls and floors by combining one or more of the compounds with soaps, detergents and cleansing agents and using the products in the conventional manner for the cleansing, sanitizing and sterilization of such surfaces and areas.

Some of the compounds, such as the products of Examples 6 and 7, are also useful insecticides and can be used to kill mosquito larvae in standing bodies of water by applying and mixing the compounds in the water at concentrations in the range of about 20 parts per million by weight.

I claim:

1. A compound of the formula

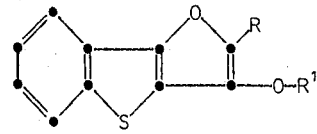

wherein R represents cyano, $C_1$–$C_2$ alkylcarbonyl or $C_1$–$C_2$ alkoxycarbonyl;
$R^1$ represents $C_1$–$C_2$ alkyl or hydrogen;
provided that $R^1$ represents hydrogen when R represents cyano or $C_1$–$C_2$ alkylcarbonyl.

2. The compound of claim 1 which is 3-hydroxy[1]-benzothieno[3,2-b]furan-2-carboxylic acid, methyl ester.

3. The compound of claim 1 which is 3-hydroxy[1]-benzothieno[3,2-b]furan-2-carbonitrile.

4. The compound of claim 1 which is 3-hydroxy[1]-benzothieno[3,2-b]furan-2-yl methyl ketone.

5. The compound of claim 1 which is 3-methoxy[1]-benzothieno[3,2-b]furan-2-carboxylic acid, methyl ester.

* * * * *